United States Patent
Coln

Patent Number: 5,804,957
Date of Patent: Sep. 8, 1998

[54] CONSTANT CURRENT SUPPLY SYSTEM FOR A VARIABLE RESISTANCE LOAD

[75] Inventor: Michael Coln, Lexington, Mass.

[73] Assignee: Analog Devices, Inc., Norwood, Mass.

[21] Appl. No.: 910,285

[22] Filed: Aug. 13, 1997

[51] Int. Cl.[6] .................................. G05F 1/56; A61N 1/18
[52] U.S. Cl. ............................................. 323/282; 607/72
[58] Field of Search ................................... 323/220, 282, 323/284, 285; 128/734, 744; 607/62, 72, 46

[56] References Cited

U.S. PATENT DOCUMENTS

| | | | |
|---|---|---|---|
| 3,991,755 | 11/1976 | Vernon et al. | 128/172.1 |
| 5,426,387 | 6/1995 | Teiland et al. | 323/283 |
| 5,571,149 | 11/1996 | Liss et al. | 607/72 |

Primary Examiner—Matthew V. Nguyen
Attorney, Agent, or Firm—Iandiorio & Teska

[57] ABSTRACT

A constant current supply system for a variable resistance load includes first and second output terminals for applying a predetermined current to a variable resistance load; a constant current circuit connected to the second output terminal for providing the predetermined current to the load; a voltage supply connected to the first terminal for providing a voltage across the terminal and constant current circuit; and a voltage supply control circuit for monitoring the voltage at the second terminal across the constant current circuit and adjusting the voltage supply to maintain the second terminal at a preselected voltage for maintaining the predetermined current to the variable resistance load.

14 Claims, 4 Drawing Sheets

CONSTANT CURRENT SUPPLY SYSTEM FOR A VARIABLE RESISTANCE LOAD

FIELD OF INVENTION

This invention relates to a constant current supply system for a variable resistance load, and more particularly to such a system for use in iontophoretic transdermal drug delivery.

BACKGROUND OF INVENTION

Iontophoresis or transdermal drug delivery is a relatively new technique which employs a small electric current to carry a drug by means of ionic flow through a patient's skin into the body. Since the dose rate is proportional to the current, the current has to be controlled extremely carefully as to magnitude and time. In some, on demand applications the patient initiates the request and the system responds with a measured dose over a predetermined time. If the patient exceeds the prescribed dosage then the system must refuse delivery. Different drugs and different applications or dosages of the same drug may require different electric currents and time schedules. These systems are battery driven and attached to the patient so they are generally desired to be small, portable and unobtrusive, such as provided by integrated circuit implementations. But they typically require large voltages on the order of ten volts to overcome the skin resistance. Such voltage levels are not conducive to present integrated circuit technology.

In one prior art approach the current control amplifier and the output pass transistor are subject to the full boosted voltage, typically on the order of 10 volts, and so they must be made off chip in a high voltage semiconductor fabrication process, or if it is to be included on the chip the entire chip control circuit must be made by such a high voltage semiconductor fabrication process. Another problem with such devices is that the patient resistance between the application electrodes can vary widely and thus the voltage across the patient will vary widely too. Therefore, any excess voltage often more than half of the boosted voltage, may appear across the pass transistor requiring it to dissipate the excess energy in the form of heat, resulting in serious reduction of efficiency and battery life.

SUMMARY OF INVENTION

It is therefore an object of this invention to provide an improved constant current supply system for a variable resistance load.

It is a further object of this invention to provide such a system for use in an iontophoretic transdermal drug delivery.

It is a further object of this invention to provide such a system which eliminates the exposure of the constant current circuit and voltage supply control circuit to the full voltage required to provide the desired current to the load.

It is a further object of this invention to provide such a system which enables the constant current circuit and voltage supply control circuit to be implemented in single, conventional, low voltage integrated circuit.

It is a further object of this invention to provide such a system in which the voltage is adjusted in accordance with the variations in the load resistance to eliminate excess voltage beyond that needed to maintain a desired current.

It is a further object of this invention to provide such a system which is more efficient, less expensive, smaller, more portable, and enables longer battery life.

The invention results from the realization that a small, portable, efficient constant current supply having extended battery life and suitable for use in an iontophoretic transdermal drug delivery system having first and second patient electrodes for delivering a predetermined current to a patient can be achieved with a constant current circuit connected to the second patient electrode, a voltage supply connected to the first patient electrode and a voltage supply control circuit for monitoring the voltage at the second electrode and adjusting the voltage supply to maintain the second electrode at a preselected voltage for maintaining the predetermined current to the patient in spite of variations in the resistance of the patient between the electrodes.

This invention features a constant current supply system for a variable resistance load including first and second output terminals for applying a predetermined current to a variable resistance load. There is a constant current circuit connected to the second output terminal for providing the predetermined current to the load and a voltage supply connected to the first terminal for providing a voltage across the terminal and constant current circuit. A voltage supply control circuit monitors the voltage at the second terminal across the constant current circuit and adjusts the voltage supply to maintain the second terminal at a preselected voltage for maintaining the predetermined current to the variable resistance load.

In a preferred embodiment the constant current circuit may include a pass transistor for conducting a predetermined current, a sensor resistor for developing a voltage representative of the predetermined current, an amplifier responsive to the voltage representative of the predetermined current, and a first reference voltage for driving the pass transistor to conduct the predetermined current. The voltage supply control circuit may include a comparator circuit responsive to the voltage across the constant current circuit and to a second reference voltage for driving the voltage supply to maintain the second terminal at the preselected voltage. The voltage supply control circuit may include a voltage limiter circuit for monitoring the voltage on the first terminal and adjusting the voltage supply to limit the voltage across the terminals from exceeding a preset limit. The voltage limiter circuit may include a voltage divider connected to the first terminal and a comparator circuit responsive to a voltage developed on the voltage divider representative of the voltage on the first terminal and to a third reference voltage for adjusting the voltage supply to prevent the voltage on the first terminal from exceeding the preset limit. The constant current circuit may include a first constant current source. The voltage limiter circuit may include a resistance connected to the first terminal, a second constant current source for maintaining a bias current in the resistance and a comparator circuit responsive to the voltage developed across the resistance and the voltage developed on the second terminal for driving the voltage supply to maintain the voltage between the terminals from exceeding a preestablished level.

The invention also features an iontophoretic transdermal drug delivery system including first and second electrodes for applying a predetermined current to a patient and a constant current circuit connected to the second electrode for providing the predetermined current to the patient. A voltage supply connected to the first electrode provides a voltage across the electrodes and constant current circuit. There is a voltage supply control circuit for monitoring the voltage at the second electrode across the constant current circuit and adjusting the voltage supply to maintain the second electrode at a preselected voltage for maintaining the predetermined current to the patient.

In a preferred embodiment the constant current circuit may include a pass transistor for conducting the predetermined current, a sense resistor for developing a voltage representative of the predetermined current and an amplifier responsive to the voltage representative of the predetermined current and a first reference voltage for driving the pass transistor to conduct the predetermined current. The voltage supply control circuit may include a comparator circuit responsive to the voltage across the constant current circuit and to a second reference voltage for driving the voltage supply to maintain the second electrode at the preselected voltage. The voltage supply control circuit may include a voltage limiter circuit for monitoring the voltage on the first electrode and adjusting the voltage supply to limit the voltage across the electrodes from exceeding a preset limit. The voltage limiter circuit may include a voltage divider connected to the first electrode and a comparator circuit responsive to the voltage developed on the voltage divider representative of the voltage on the first electrode and to a third reference voltage for adjusting the voltage supply to prevent the voltage on the first electrode from exceeding the preset limit. The constant current circuit may include a first constant current source. The voltage limiter circuit may include a resistance connected to the first electrode, a second constant current source for maintaining a bias current in the resistance and a comparator circuit responsive to the voltage developed across the resistance and the voltage developed on the second electrode for driving the voltage supply to maintain the voltage between the electrodes from exceeding a preestablished level.

DISCLOSURE OF PREFERRED EMBODIMENT

Other objects, features and advantages will occur to those skilled in the art from the following description of a preferred embodiment and the accompanying drawings, in which.

Figure 1:
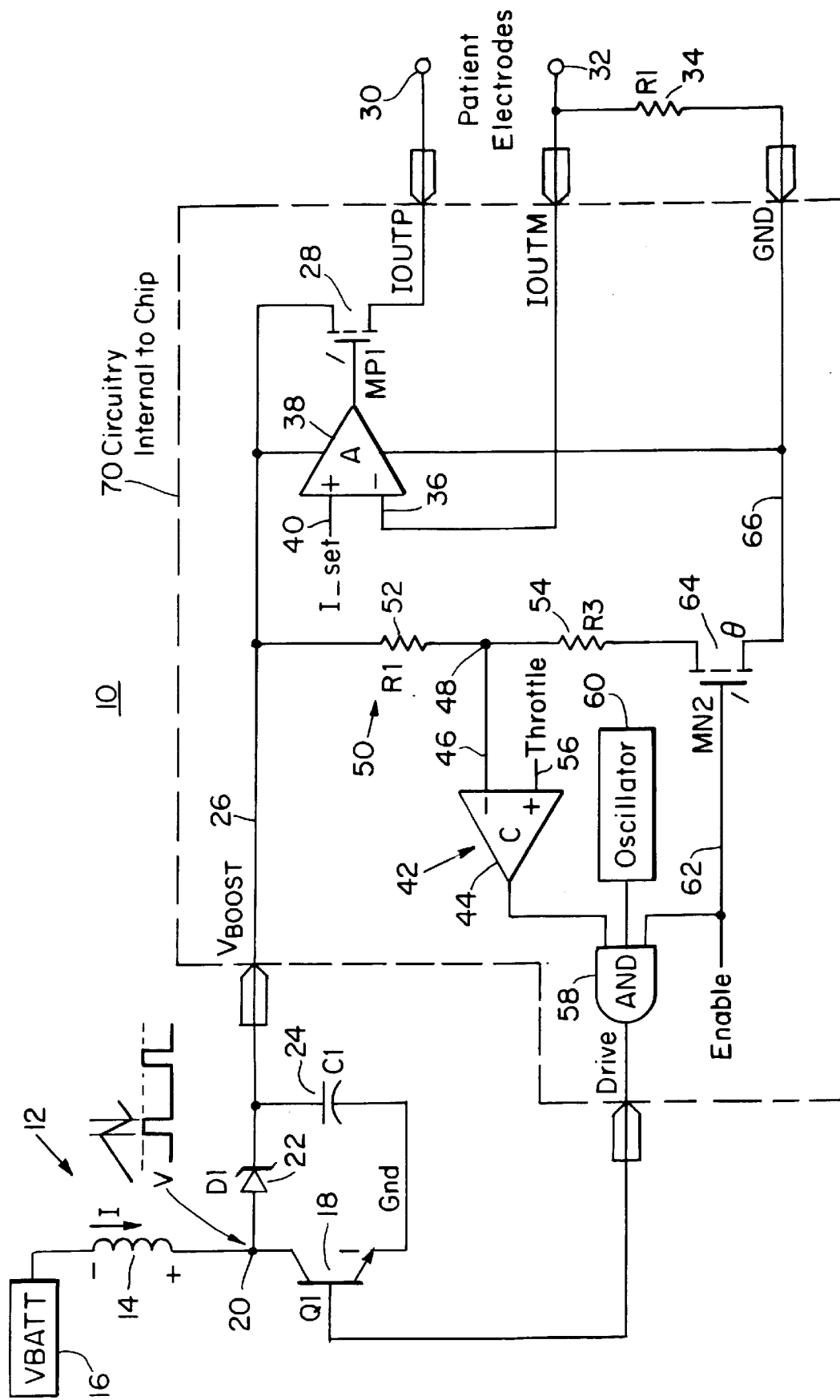
FIG. 1 is a schematic diagram of a prior art constant current supply system employed in an iontophoretic transdermal drug delivery system.

There is shown in FIG. 1 a prior art constant current supply system for a variable resistance load 10 for use in an iontophoretic transdermal drug delivery system. There is a fly back switching voltage supply 12 including inductance 14 which responds to a low voltage battery 16 such as a three volt lithium battery to provide a current through transistor 18. When transistor 18 is on the voltage at point 20 approaches ground. The lagging current I through the conductor ramps up, storing energy in the magnetic field of inductor 14. When transistor 18 is turned off the collapsing magnetic field of inductor 14 provides a high voltage at point 20 which is rectified through diode 22 and stored in capacitor 24. This high voltage or boosted voltage $V_{BOOST}$ appears on line 26 and is delivered through pass transistor 28 to the first terminal or patient electrode 30. The current between first terminal 30 and the second terminal or patient electrode 32 is usually in the neighborhood of a fraction of a milliamp and the voltage across it is typically approximately 10 volts. The current flowing between electrodes 30 and 32 develops a voltage across resistance 34. That voltage, representing the current flow between electrodes 30 and 32, is delivered to one input 36 of amplifier 38. The other input 40 to amplifier 38 is a reference voltage which represents the current desired to flow through pass transistor 28 and patient electrodes 30 and 32.

The switching on and off of transistor 18 is controlled by feedback circuit 42 which includes comparator 44 having at one input 46 the voltage from point 48 in voltage divider 50 formed of series resistances 52 and 54. Typically with $V_{BOOST}$ on line 26 at ten volts the drop across resistance 52 is eight volts and so the voltage on point 48 at input 46 is two volts. The reference input 56 is maintained at the desired voltage, in this example two volts, so that any time the voltage at point 48 drops below two volts comparator 44 provides an output to AND gate 58. In order for AND gate to pass through the square wave pulses from oscillator 60 it is necessary that a third input from enable line 62 be present. Thus whenever the circuit is desired to be enabled and comparator 44 shows that the voltage at point 48 is below two volts, the square wave pulses from oscillator 60 will pass through AND gate 50 to turn on and off transistor 18. As the square wave voltage pulses are boosted by the action of inductance 14 the voltage in capacitor 24 rises; thus the $V_{BOOST}$ on line 26 rises and point 48 approaches two volts, at which point comparator 44 will turn off.

The signal on enable line 62 also operates anti-leakage transistor 64 which is driven by the enable circuit on line 62 to provide a path from $V_{BOOST}$ on line 26 through voltage divider 50 to ground 66. However, when the enable signal is not present on line 62 transistor 64 provides an open circuit which prevents leakage from inductance 14 through diode 22 in voltage divider 50.

This prior art circuit has a number of shortcomings. First, since amplifier 38 and pass transistor 28 are directly subject to the high voltage $V_{BOOST}$ of for example 10 volts on line 26, they must be made by a high voltage fabrication process which is more expensive than the normal IC fabrication process, and since they are on the same chip 70 as the other components the entire system must be made by that more expensive fabrication process if it is to be integrated in the smallest possible package. Another problem with this prior art circuit is that the resistance between the patient electrodes 30 and 32, that is, the resistance of the patient's skin, can vary widely. So while normally only two or three volts may be necessary across electrodes 30 and 32 the voltage needed may be greater and may even approach the full ten volts of $V_{BOOST}$ at the initial application of the electrodes 30 and 32 to the skin and at various other times for other reasons. This requires pass transistor 28 in most cases to absorb half or more of $V_{BOOST}$ thereby dissipating through heat the excess energy not required in the voltage across patient electrodes 30 and 32. This makes the system inefficient and requires a larger battery and results in shorter battery life.

Figure 2:
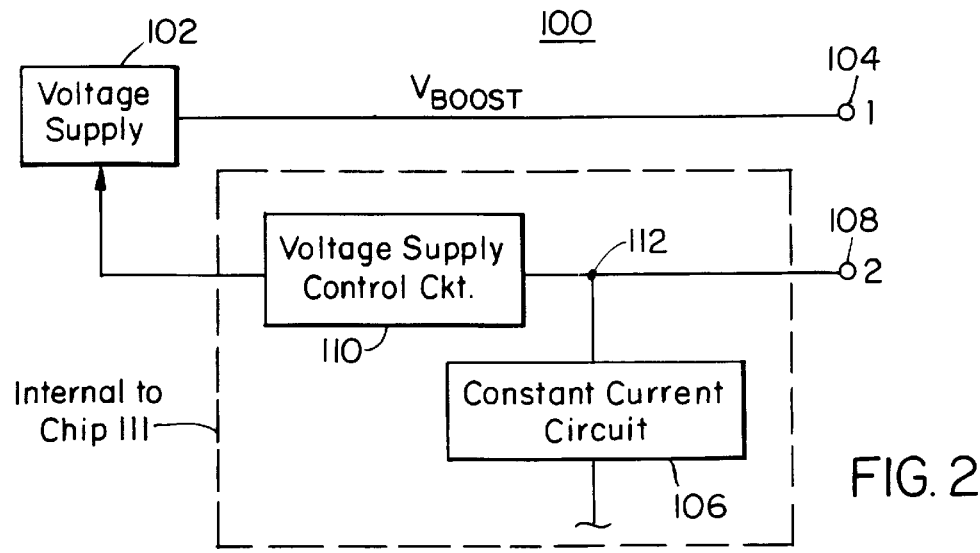
FIG. 2 is a simplified block diagram of a constant current supply system for a variable resistance load according to this invention.

In accordance with this invention a constant current supply system 100, FIG. 2, includes a voltage supply 102 which directly feeds the first terminal or patient electrode 104. The constant current circuit 106, however, is not subject to the high $V_{BOOST}$ voltage at electrode 104. Rather, it sees the lower voltage at electrode 108 after the drop through the patient's skin. This means that the constant current circuit 106 can be made of conventional low voltage integrated circuit components. So too is the case with voltage supply control circuit 110 which senses the voltage at point 112 across constant current circuit 106 and drives voltage supply 102 to keep $V_{BOOST}$ on electrode 104 at a sufficiently high voltage to maintain the voltage at point 112 so that the desired constant current 106 flows through electrodes 104 and 108. Since neither voltage supply control circuit 110 nor constant current circuit 106 are subject to the elevated voltage $V_{BOOST}$ at electrode 104 they may be made by conventional integrated circuit fabrication techniques and all mounted on a single conventional chip 111.

Figure 3:
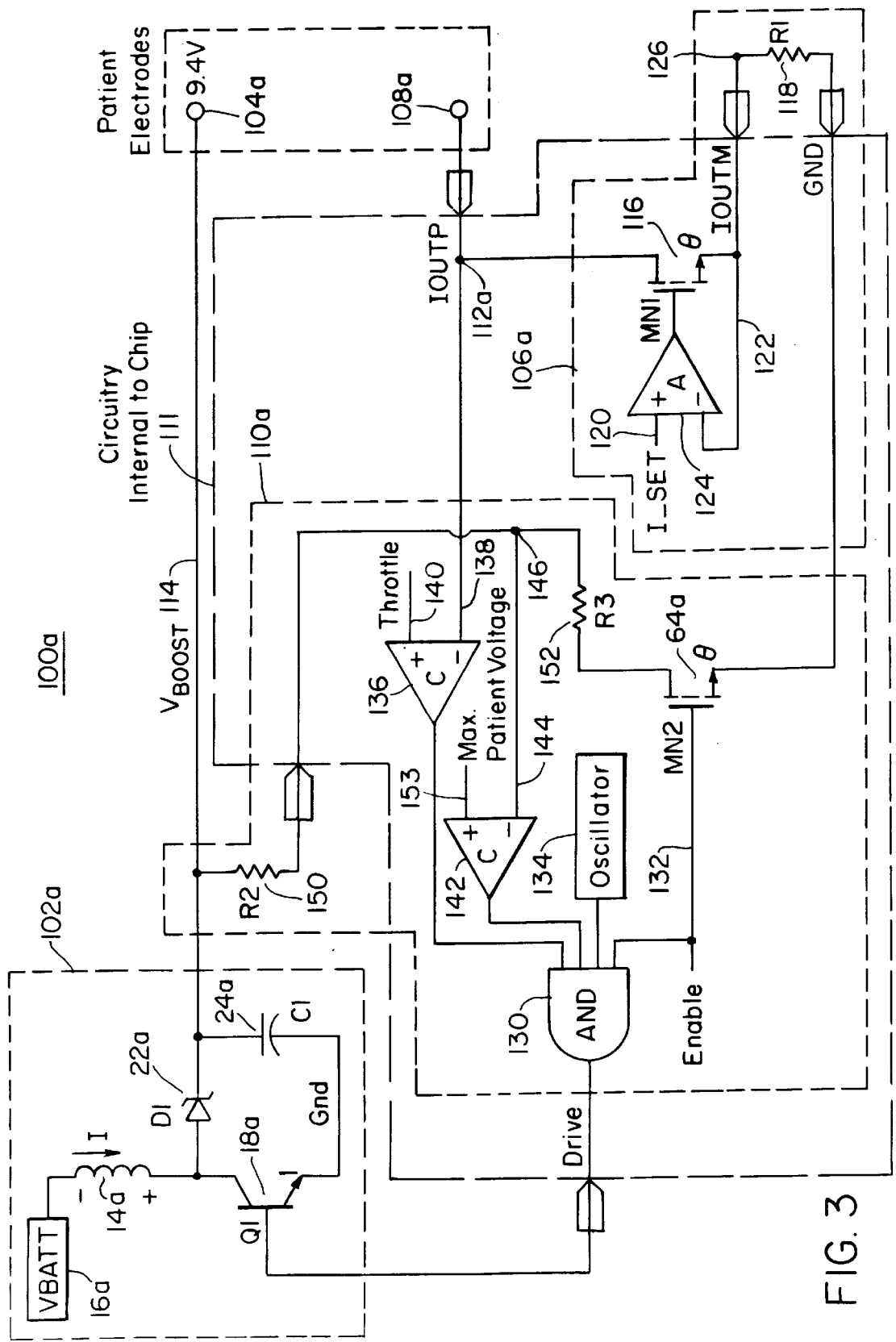
FIG. 3 is a more detailed schematic diagram of one embodiment of the system of FIG. 2 employed in an iontophoretic transdermal drug delivery system.

In one embodiment the constant current supply system 100a, FIG. 3, shown in FIG. 2 can be implemented using a voltage supply 102a which is a fly back switching supply similar to fly back switching supply 12 in FIG. 1. Fly back switching supply 102a provides an elevated voltage $V_{BOOST}$ on line 114 to first electrode 104a. Constant current circuit 106a includes pass transistor 116 which interconnects second electrode 108a through resistance 118 to ground. The current through pass transistor 116 is chosen for a predetermined value, typically a half milliamp or less. When the system is used in an iontophoretic transdermal drug delivery system, the particular drug and therapy prescribed will determine that current. Whatever that current may be its flow through resistor 118 develops a voltage across resistor 118 at point 126 which is delivered to one input 122 of amplifier 124. The other input 120 is set to a preselected voltage which represents the desired current flow through electrodes 104a, 108a and pass transistor 118. In this way the current through electrodes 104a and 108a is fixed.

Voltage supply control circuit 110a includes four input AND gate 130 which receives one input from enable line 132 and another input from square pulse oscillator 134. The third input is delivered from comparator 136 which receives at one input 138 the voltage at point 112a on the second patient electrode 108a. The other input 140 to comparator 136 is set to a preselected voltage which represents the voltage desired at point 112a. Thus if the voltage at point 112a is equal to or greater than the voltage at input 140 comparator 136 provides no output. However, if the voltage at point 112a drops below that on input 140 then comparator 136 provides an output to the third input of AND gate 130.

Since the variable resistance that may occur between patient electrodes 104 and 108a may drive the $V_{BOOST}$ voltage on line 114 to elevated levels and since at elevated levels the voltage may cause discomfort or annoyance in the patient, another comparator 142 is provided to limit the maximum voltage to which $V_{BOOST}$ on line 114 is permitted to rise. Comparator 142 has one input 144 connected to point 146 of voltage divider 148 which includes resistance 150 in series with resistance 152. Thus when an enable signal on line 132 is present and comparator 136 indicates that the voltage at point 112a is below the desired level, and comparator 142 indicates that the drop across resistance 150 as reflected by the voltage at point 146 is below the reference voltage at input 153 of comparator 142, comparator 142 also provides an output. Being in receipt of all four inputs AND gate 130 provides an output to turn on transistor 18a in power supply 102a. Thus in this embodiment according to this invention pass transistor 116 is not required to absorb a large voltage drop with the attendant heat dissipation and loss of efficiency.

Amplifier 124 and pass transistor 116 as well as all the other components, comparators 136, 142, oscillator 134 and AND gate 130, are all isolated from the high voltage of $V_{BOOST}$ on line 114, and so they may all be made by a conventional low voltage integrated circuit fabrication technique and may all be included on a single conventional integrated circuit chip 111. Throughout the figures like parts have been given like numbers and similar parts like numbers primed or accompanied by one or more lower case letters.

In system 100a, FIG. 3, as the resistance between patient electrodes 104a and 108a increases beyond the point that comparator 136 ceases to provide an output, the voltage at point 112a must decrease. As it decreases the current through pass transistor 116 will also decrease so that gradually the current will be reduced to zero or nearly zero. This means that if this system is used in an iontophoretic transdermal drug delivery system, for example, the amount of the drug introduced into the patient will decrease in a similar fashion.

Figure 5:
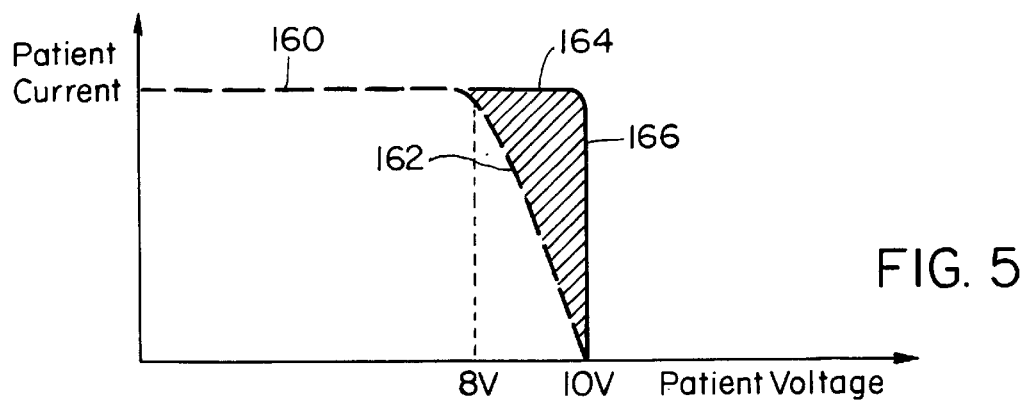
FIG. 5 is an illustration of the variation of the full voltage with respect to patient current for the embodiments of FIGS. 3 and 4.
Figure 4:
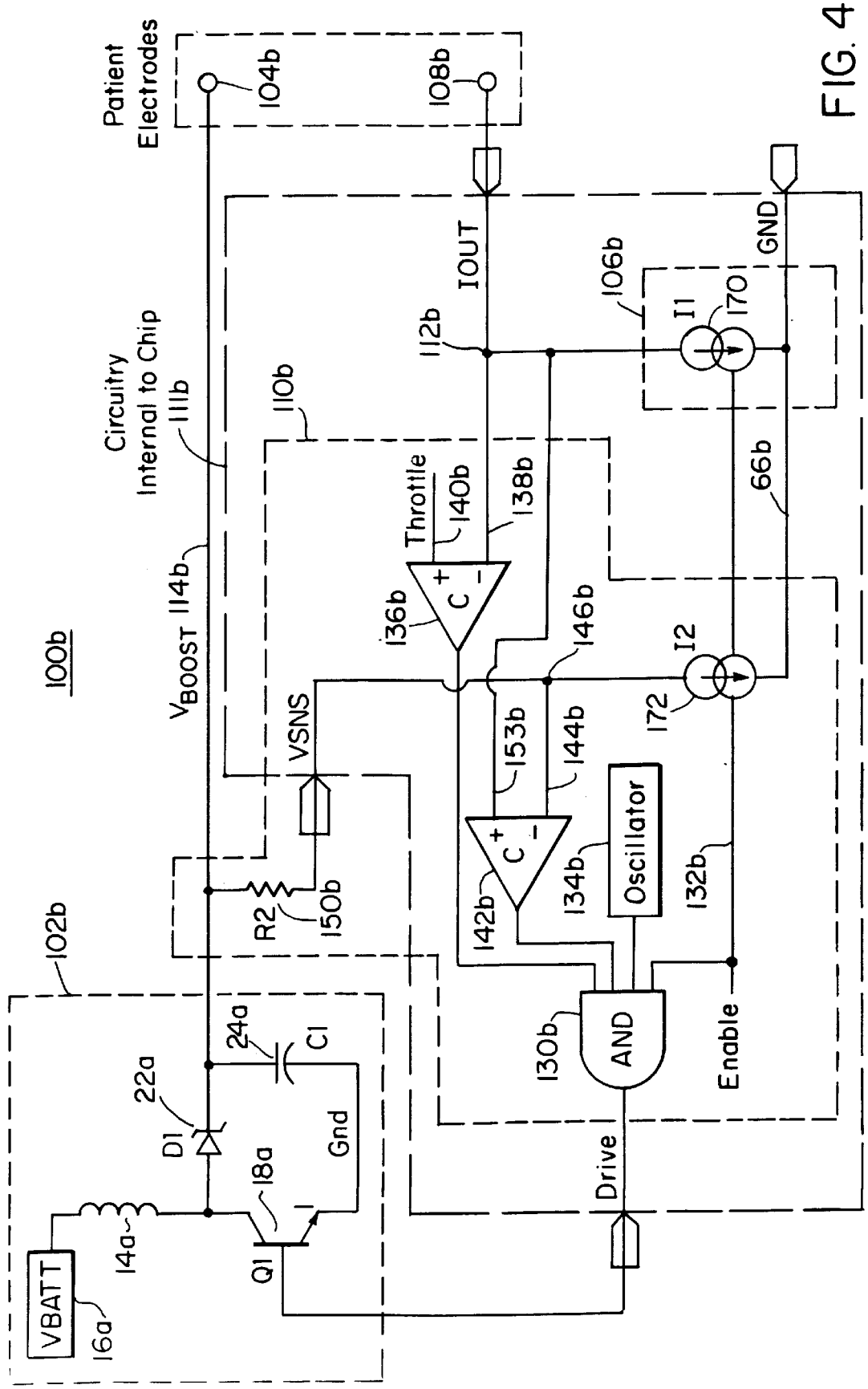
FIG. 4 is a schematic diagram similar to FIG. 3 of another embodiment of the system of FIG. 2.

This is not the case in the embodiment 100b, FIG. 4, where input 153b of comparator 142b instead of being connected to a reference is connected directly to point 112b at second electrode 108b and at the input 138b to comparator 136b. In this configuration the patient current or the current between patient electrodes 104b and 108b continues at the same level even though the resistance of the patient between electrodes 104b and 108b is increasing, so that the proper current and the proper drug dosage can be continued even though the voltage is varying until the point at which comparator 142b will no longer allow the elevated voltage $V_{BOOST}$ on line 114b to increase any further. This is shown in FIG. 5, where a plot of the patient current on the ordinate and the patient voltage on the abscissa shows that the circuit 100a of FIG. 3 follows the path 160 indicated in dashed lines wherein the current falloff 162 beginning at approximately eight volts is quite gradual with increasing patient voltage, whereas the solid line representation 164 of the patient current in system 100b of FIG. 4, continues more nearly constant until it abruptly falls off 166 at the maximum limit of ten volts.

Also in FIG. 4, constant current circuit 106b now takes the form of a constant current source 170 and resistance 152 is replaced by a second constant current source 172 which actually obviates the need for anti-leakage transistor 64a.

Figure 6:
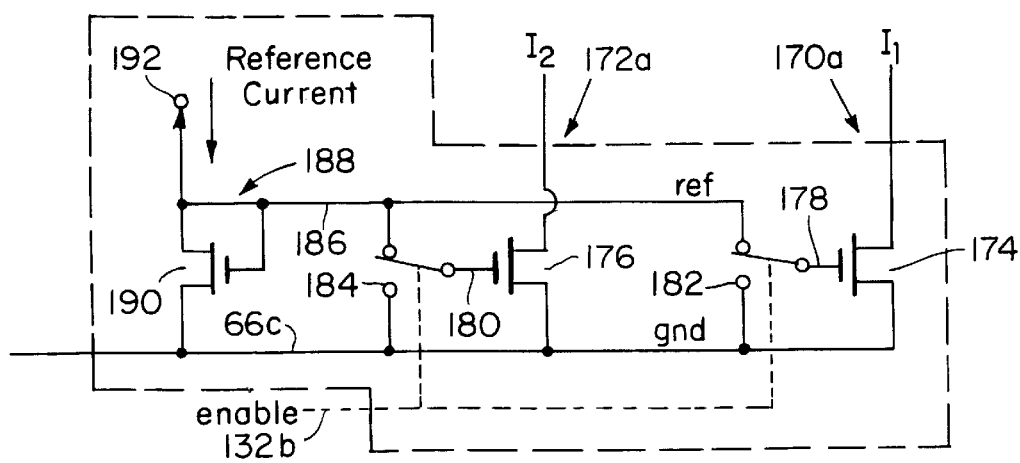
FIG. 6 is a schematic block diagram showing one implementation of the constant current sources of FIG. 4.

Constant current sources 170, 172 may be implemented as shown with conventional current sinks 170a, 172a, FIG. 6, in which each includes a transistor 174, 176 with its base 178, 180 selectively connected to either ground 182, 184 or a reference current on line 186 from reference current source 188 which includes a transistor 190 connected to a reference current at terminal 192.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A constant current supply system for a variable resistance load, comprising:

first and second output terminals for applying a predetermined current to a variable resistance load;

a constant current circuit connected to a second output terminal for providing said predetermined current to the load;

a voltage supply connected to said first terminal for providing a voltage across said terminals and constant current circuit; and a voltage supply control circuit for monitoring the voltage at said second terminal across said constant current circuit and adjusting said voltage supply to maintain said second terminal at a preselected voltage for maintaining said predetermined current to said variable resistance load.

2. The constant current supply system of claim 1 in which said constant current circuit includes a pass transistor for conducting said predetermined current, a sense resistor for developing a voltage representative of said predetermined current and an amplifier responsive to said voltage representative of said predetermined current and a first reference voltage for driving said pass transistor to conduct said predetermined current.

3. The constant current supply system of claim 1 in which said voltage supply control circuit includes a comparator circuit responsive to the voltage across the constant current circuit and to a second reference voltage for driving said voltage supply to maintain said second terminal at said preselected voltage.

4. The constant current supply system of claim 1 in which said voltage supply control circuit includes a voltage limiter circuit for monitoring the voltage on said first terminal and adjusting said voltage supply to limit the voltage across said terminals from exceeding a preset limit.

5. The constant current supply system of claim 4 in which said voltage limiter circuit includes a voltage divider connected to said first terminal and a comparator circuit responsive to a voltage developed on said voltage divider representative of the voltage on said first terminal and to a third reference voltage for adjusting said voltage supply to prevent the voltage on said first terminal from exceeding said preset level.

6. The constant current supply system of claim 4 in which said constant current circuit includes a first constant current source.

7. The constant current supply system of claim 4 in which said voltage limiter circuit includes a resistance connected to said first terminal, a second constant current source for maintaining a bias current in said resistance and a comparator circuit responsive to the voltage developed across said resistance and the voltage developed on said second terminal for driving said voltage supply to maintain the voltage between said terminals from exceeding a preestablished level.

8. An iontophoretic transdermal drug delivery system comprising:

first and second electrodes for applying a predetermined current to a patient;

a constant current circuit connected to said second electrode for providing said predetermined current to the patient;

a voltage supply connected to said first electrode for providing a voltage across said electrodes and constant current circuit; and a voltage supply control circuit for monitoring the voltage at said second electrode across said constant current circuit and adjusting said voltage supply to maintain said second electrode at a preselected voltage for maintaining said predetermined current to the patient.

9. The iontophoretic transdermal drug delivery system of claim 8 in which said constant current circuit includes a pass transistor for conducting said predetermined current, a sense resistor for developing a voltage representative of said predetermined current and an amplifier responsive to said voltage representative of said predetermined current and a first reference voltage for driving said pass transistor to conduct said predetermined current.

10. The iontophoretic transdermal drug delivery system of claim 8 in which said voltage supply control circuit includes a comparator circuit responsive to the voltage across the constant current circuit and to a second reference voltage for driving said voltage supply to maintain said second electrode at said preselected voltage.

11. The iontophoretic transdermal drug delivery system of claim 8 in which said voltage supply control circuit includes a voltage limiter circuit for monitoring the voltage on said first electrode and adjusting said voltage supply to limit the voltage across said electrodes from exceeding a preset limit.

12. The iontophoretic transdermal drug delivery system of claim 11 in which said voltage limiter circuit includes a voltage divider connected to said first electrode and a comparator circuit responsive to a voltage developed on said voltage divider representative of the voltage on said first electrode and to a third reference voltage for adjusting said voltage supply to prevent the voltage on said first electrode from exceeding said preset level.

13. The iontophoretic transdermal drug delivery system of claim 8 in which said constant current circuit includes a first constant current source.

14. The iontophoretic transdermal drug delivery system of claim 11 in which said voltage limiter circuit includes a resistance connected to said first electrode, a second constant current source for maintaining a bias current in said resistance and a comparator circuit responsive to the voltage developed across said resistance and the voltage developed on said second electrode for driving said voltage supply to maintain the voltage between said electrodes from exceeding a preestablished level.

* * * * *